(12) United States Patent
Voegele et al.

(10) Patent No.: US 8,849,377 B2
(45) Date of Patent: Sep. 30, 2014

(54) INTRALUMINAL TISSUE MARKERS

(75) Inventors: James W. Voegele, Cincinnati, OH (US);
William B. Weisenburgh, II,
Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1425 days.

(21) Appl. No.: 12/041,362

(22) Filed: Mar. 3, 2008

(65) Prior Publication Data

US 2009/0221913 A1 Sep. 3, 2009

(51) Int. Cl.
*A61B 6/00* (2006.01)
*A61B 19/00* (2006.01)
*A61B 17/00* (2006.01)

(52) U.S. Cl.
CPC ....... *A61B 19/54* (2013.01); *A61B 2017/00867* (2013.01)
USPC .......................................... 600/431; 128/899

(58) Field of Classification Search
CPC .............. A61B 19/54; A61B 2019/54; A61B 2019/5404; A61B 2019/5408; A61B 2019/5412; A61B 2019/5437; A61B 2019/5462; A61B 2019/5487; A61B 2019/5491
USPC .............. 600/431; 128/897–899, 407–411, 128/414–417, 420–427, 429–435
See application file for complete search history.

(56) References Cited

U.S. PATENT DOCUMENTS

| | | | | |
|---|---|---|---|---|
| 5,782,903 A | * | 7/1998 | Wiktor | 623/1.22 |
| 6,220,248 B1 | * | 4/2001 | Voegele et al. | 128/898 |
| 6,228,055 B1 | * | 5/2001 | Foerster et al. | 604/116 |
| 6,371,904 B1 | * | 4/2002 | Sirimanne et al. | 600/3 |
| 2002/0107437 A1 | * | 8/2002 | Sirimanne et al. | 600/407 |
| 2003/0225420 A1 | * | 12/2003 | Wardle | 606/151 |
| 2005/0182318 A1 | * | 8/2005 | Kaji et al. | 600/424 |

FOREIGN PATENT DOCUMENTS

WO WO2007/035798 * 3/2007 ............ A61M 25/09

* cited by examiner

*Primary Examiner* — Samuel Gilbert
*Assistant Examiner* — Carrie R Dorna
(74) *Attorney, Agent, or Firm* — Mintz Levin Cohn Ferris Glovsky and Popeo, P.C.

(57) ABSTRACT

Methods and devices are provided for marking tissue to be subsequently located for removal from a body or for other examination. In general, a marker is provided that can be delivered adjacent to tissue desirable for marking. The marker can coil adjacent to the desired tissue. The marker can remain disposed in the body in its coiled position and be subsequently palpably identified and/or visually identified to locate the desired tissue.

13 Claims, 5 Drawing Sheets

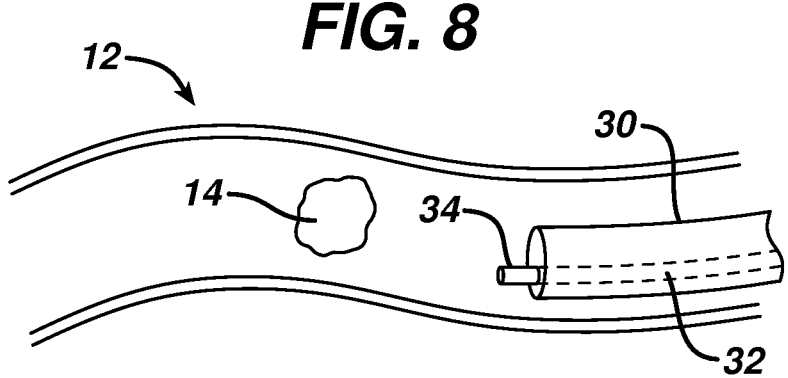
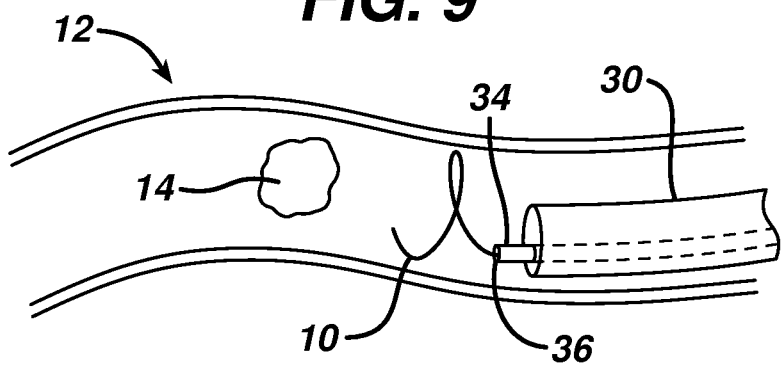
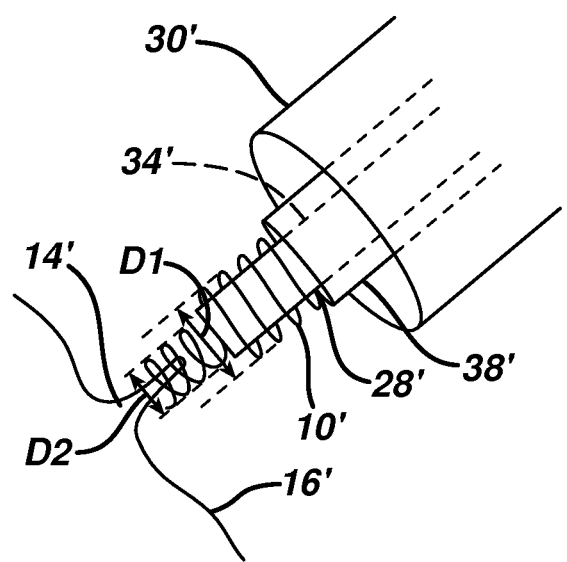

INTRALUMINAL TISSUE MARKERS

FIELD OF THE INVENTION

The present invention relates to intraluminal tissue markers and methods for marking tissue intraluminally.

BACKGROUND OF THE INVENTION

Colonoscopy is an outpatient procedure in which the rectum and the inside of the lower large intestine (colon) are examined. Colonoscopies are commonly used to evaluate bowel disorders, rectal bleeding or polyps (usually benign growths) found on contrast x-rays. Colonoscopies are also performed to screen people over age 50 for colon and rectal cancer. During a colonoscopy, a physician uses a colonoscope (a long, flexible instrument about ½ inch in diameter) to view the lining of the colon. The colonoscope is inserted through the rectum and advanced to the large intestine.

If necessary during a colonoscopy, small amounts of tissue can be removed for analysis (called a biopsy) and polyps can be identified and removed. In many cases, colonoscopy allows accurate diagnosis and treatment without the need for a major operation. However, in some cases the tissue cannot be removed during the colonoscopy and thus must be removed in a subsequent surgical procedure. In these situations, india ink or blue dye is topically injected during the preoperative colonoscopy to mark the tumor site. However, such a procedure includes the intrinsic danger of possibly injecting dye into the peritoneal cavity. In addition, the injected marker may also spread so widely that the intended site may become obscured.

Accordingly, there remains a need for improved methods and devices for marking tissue, such as the bowel wall.

SUMMARY OF THE INVENTION

The present invention generally provides methods and devices for marking tissue to be subsequently located for removal from a body or for other examination. In one aspect, a method for marking tissue is provided that includes advancing a delivery device into a body lumen and advancing a marker from the delivery device to deliver the marker into the body lumen. The delivery device can be introduced to the body lumen in a variety of ways. For example, the delivery device can be introduced to the body lumen through a cannula (e.g., a colonoscope) having a working channel extending into the body lumen. In some embodiments, the marker can be delivered proximate to tissue to be removed from the body lumen. The marker can move from an expanded position to a coiled position as it is advanced from the delivery device to form a coil that engages the body lumen. The coil can engage the body lumen in any way, such as by being positioned to extend around an inner wall of the body lumen, on an inner surface of the body lumen proximate to a tissue growth on the body lumen or around a tissue growth. The method can also include removing the delivery device from the body lumen and leaving the marker in the coiled position inside the body lumen. The method can further include identifying the marker in the coiled position in the body lumen to locate tissue to be removed from the body lumen. Locating tissue to be removed can include, for example, visually identifying the marker and/or palpably identifying the marker.

In another aspect, a method for marking tissue is provided that includes advancing a marker along a delivery device disposed adjacent to tissue to advance the marker off of a distal end of the delivery device. The marker can coil as it is removed from the delivery device to engage tissue proximate to tissue to be removed from the body. The marker can coil in a variety of positions. For example, the marker can coil to extend around an inner wall of a tubular structure or the marker can coil to at least partially extend around tissue to be removed from the body or from a surface of an organ. In some embodiments, the method can also include determining a location of the coiled marker by palpably manipulating the tissue.

In another embodiment, a tissue marking system is provided and includes a delivery device (e.g., an endoscope or laparoscope) configured to be disposed adjacent to tissue in a body and a marker disposed in the delivery device in an expanded position and configured to move to a coiled position as it is advanced from the delivery device to engage the tissue. The delivery device can be introduced into a body in a variety of ways. For example, the delivery device can be disposed through a natural orifice or inserted through a puncture hole formed in tissue. In some embodiments, the marker in the coiled position can engage an inner diameter of a body lumen. The marker can have a variety of configurations and be made from a variety of materials. For example, the marker can be a spring, and/or it can be formed from a shape memory material.

BRIEF DESCRIPTION OF THE DRAWINGS

The invention will be more fully understood from the following detailed description taken in conjunction with the accompanying drawings, in which:

FIG. 8 is a perspective view of one embodiment of an introducer disposed within a body lumen and having the delivery device and the marker of FIG. 5 disposed therein for delivering the marker to the body lumen;

FIG. 9 is a perspective view of the introducer and the delivery device of FIG. 8 showing the marker being advanced from the delivery device;

FIG. 10 is a perspective view of another embodiment of an introducer and a delivery device having a marker disposed therearound, showing the marker coiling around a tissue;

DETAILED DESCRIPTION OF THE INVENTION

Figure 1:
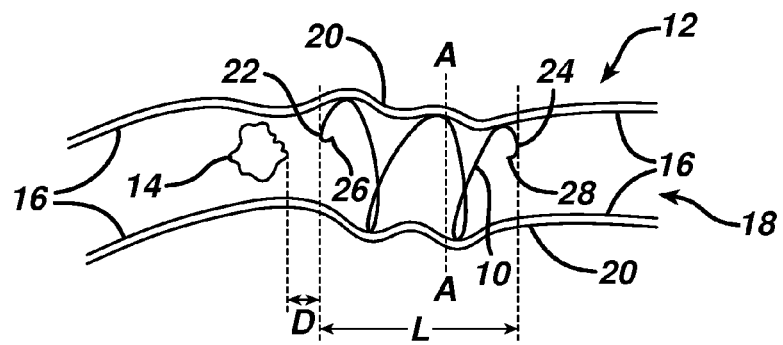
FIG. 1 is a perspective transparent view of one embodiment of a marking device disposed in a body lumen.
Figure 2:
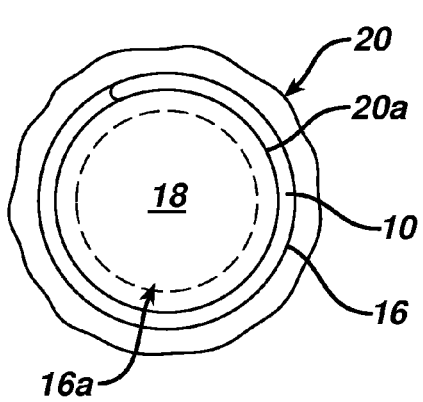
FIG. 2 is a cross-sectional view of the marking device and the body lumen of FIG. 1 taken across line A-A.
Figure 3:
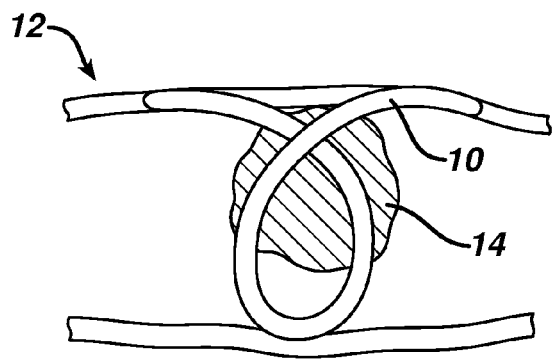
FIG. 3 is a transparent perspective view of another embodiment of a marking device disposed in a body lumen.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides methods and devices for marking tissue to be subsequently located for removal from a body or for other examination. While the methods and devices disclosed herein can be used in conventional, open surgical procedures, they are particularly useful in minimally invasive surgical procedures, particularly hand assisted laparoscopic surgery (HALS) and endoscopic procedures. The principles described herein can be applicable to the particular types of tools described herein and to a variety of other surgical tools having similar functions. In addition, the tools can be used alone in a surgical procedure, or they can be used in conjunction with other devices that facilitate minimally invasive surgical procedures. A person skilled in the art will appreciate that the present invention has application in conventional endoscopic and open surgical instrumentation as well application in robotic-assisted surgery.

In general, a marker is provided that can be delivered adjacent to tissue desirable for marking. In an exemplary embodiment, the marker can be configured to coil adjacent to the desired tissue. The term "adjacent" as used herein is intended to encompass placement on and/or placement near a desired tissue. The marker can remain disposed in the body in its coiled position, and it can be subsequently palpably identified and/or visually identified to locate the desired tissue. While the marker can be used to mark any tissue for any purpose, in an exemplary embodiment the marker is configured for delivery through the working channel of a delivery device and for use in marking tissue for removal from the body, e.g., a polyp or other tissue growth identified during a colonoscopy and intended to be removed from the colon wall during a subsequent surgical procedure.

The marker can be formed from a variety of materials but is preferably formed from a biocompatible material safe for use in the body. In an exemplary embodiment, the marker is made from a flexible elastic material, and more preferably from a shape memory material, such as Nitinol (a nickel-titanium alloy), but the marker can be made from any type of material and any combination of materials able to provide structure to the marker and appropriate for use in the body. Other exemplary shape memory metallic materials include alloys such as copper-zinc-aluminum-nickel, copper-aluminum-nickel, and nickel-titanium. Additional exemplary non-metallic shape memory materials include thermoplastic materials such as Nylon or Nylon blends and shape memory polymers such as Veriflex™. The marker can also be formed from a bioabsorbable, biocompatible material, such as polydioxanone (PDO or PDS), Vicryl™, and polylactic acid (PLA). However, it is understood that other suitable biocompatible and optionally bioabsorbable polymers can also be used for the marker. The marker can optionally have a drug coating, similar to a drug-eluting stent, that can break down over time to release a drug to, for example, help reduce chances of cell proliferation (e.g., hyperplasia) or reduce other possible adverse effects from the presence of the marker in the body. The marker can have any coloration, such as a dark color (e.g., dark blue, black, etc.) to help enhance its visibility when disposed in a body.

The marker can have any configuration. In an exemplary embodiment shown in FIGS. 1-4, the marker 10 is in the form of a spring that is movable between an expanded position, in which the spring has a substantially linear elongated configuration for delivery through a relatively small diameter working channels, and a delivered position, in which the spring is configured to engage tissue. The spring can have any shape that allows it to move between the expanded and delivered positions. For example, the spring, when in the delivered position, can be in the form of a coil or helical spring having a cylindrical shape as shown in FIG. 1, although the spring can have other shapes, such as conical or dual conical, and have individual coils of any shape, such as elliptical or rectangular. Other examples of the spring include an elastic band/thread/cord, a bellows, a volute spring, and other similar types of flexible elastic objects.

The marker 10 can be configured to be palpably identified (e.g., located by touch) through tissue, for example by touching an outer surface 20 of a body lumen 12 in which the marker 10 has been disposed, thus allowing the location of a tissue 14 desired for removal and/or other examination to be determined. The marker 10 can also or instead be configured to be visually identified in the body lumen 12. Visual observation of the marker 10 can include observing one or more ridges along the body lumen's outside surface 20, viewing still or moving images obtained by a scoping device disposed within the body lumen 12, viewing an x-ray, viewing a barium image, viewing interaction with magnetic particles (if the marker 10 includes a magnetized component), tracing radiopharmaceuticals, etc.

In the embodiment illustrated in FIG. 1, the body lumen 12 is the lower large intestine, and the tissue 14 includes a lesion, a polyp, or an unhealthy section of the bowel wall. However, the marker 10 can be disposed adjacent to any tissue anywhere within the body, e.g., within a tubular structure (such as the body lumen 12), on a surface of an organ, etc. The marker 10 has approximately two coils as illustrated in FIG. 1, but the marker 10 can have any number of coils in its coiled position (e.g., one, two, ten, etc.). Generally, the more coils the marker 10 has, the easier the marker 10 can be palpably identified because more ridges (e.g., protrusions and depressions) formed by the marker's expansion inside the body lumen 12 can be felt on the body lumen's outer surface 20 and/or because the marker 10 extends for a longer length L in its coiled position. As mentioned above, the marker 10 can additionally or alternatively be visually identified in the body lumen 12, and more coils can also allow for easier visual identification of the marker.

The length L of the marker 10 in its coiled position extends between distal-most and proximal-most portions 22, 24 of the marker 10. The distal-most and proximal-most portions 22, 24 may or may not correspond to the marker's distal and proximal ends 26, 28 when the marker 10 is in its coiled position, depending on the orientation of the marker 10 in the coiled position and/or on the configuration of the marker's distal and proximal ends 26, 28, e.g., if the marker's distal and proximal ends 26, 28 are biased to coil inwards away from the body lumen's inner wall 16 so as to reduce chances of the marker's distal and proximal ends 26, 28 cutting, puncturing, or otherwise harming the body lumen 12. Furthermore, one or both of the marker's distal and proximal ends 26, 28 can be blunted (e.g., be rounded or include a ball-like element coupled thereon) to help reduce trauma to the body lumen 12.

The marker 10 can also have any shape and size that allows it to engage tissue. As shown in FIG. 1, the marker 10 has a coiled shape when disposed within the body lumen 12 adjacent to the tissue 14 to be removed or otherwise examined. The marker 10 can have a maximum diameter in its coiled position that is greater than an inner diameter of the body lumen 12. In this way, the marker 10 can expand to extend around the inner wall 16 of the body lumen 12 so as to not substantially obstruct the body lumen's inner pathway 18, thereby allowing for normal functioning of the body lumen 12 when the marker 10 is disposed therein. In other words, the body lumen 12 can take the shape of the marker 10 for about the length L of the marker 10 in the coiled position. For example, as shown in cross-section A-A in FIG. 2, the marker 10 extends along the body lumen's inner wall 16 and expands the inner wall 16 and the outer surface 20 of the body lumen 12, leaving the body lumen's inner pathway 18 substantially unobstructed and possibly with a larger diameter than before the marker's insertion along the length L of the marker 10. For comparison, FIG. 2 also illustrates the body lumen's inner wall 16a and outer surface 20a in unexpanded, non-marked positions where they each have smaller diameters than when the marker 10 is coiled within the body lumen 12.

The marker 10 can have any cross-sectional area and any cross-sectional shape. A cross-sectional shape having at least one substantially flattened surface, such as a substantially rectangular cross-sectional shape or a semi-circular cross-sectional shape, can provide a greater bearing area between the marker 10 and the body lumen's inner wall 16 than other cross-sectional shapes, such as a substantially rounded cross-sectional shape, when at least one substantially flat-sided surface aligns with the body lumen's inner wall 16.

As mentioned above, the marker 10 can be disposed adjacent to the tissue 14 desired for marking, which includes disposal at a location where the marker 10 directly engages the tissue 14 and/or at a location where the marker 10 engages the body lumen 12 at a location proximate to the tissue 14. As illustrated in FIG. 1, the distal-most portion 22 of the marker 10 is disposed proximate to the tissue 14 at a distance D from the tissue 14. The distance D can be zero or have any positive value, although the distance D is preferably of a value small enough such that any incision into or any examination of the body lumen 12 at the location of the marker 10 allows for relatively easy identification of the tissue 14. For example, as shown in another embodiment of marker placement in FIG. 3, the distance D can be zero with the marker 10 both directly engaging the tissue 14 and engaging the body lumen 12 proximate to the tissue 14.

Figure 4:
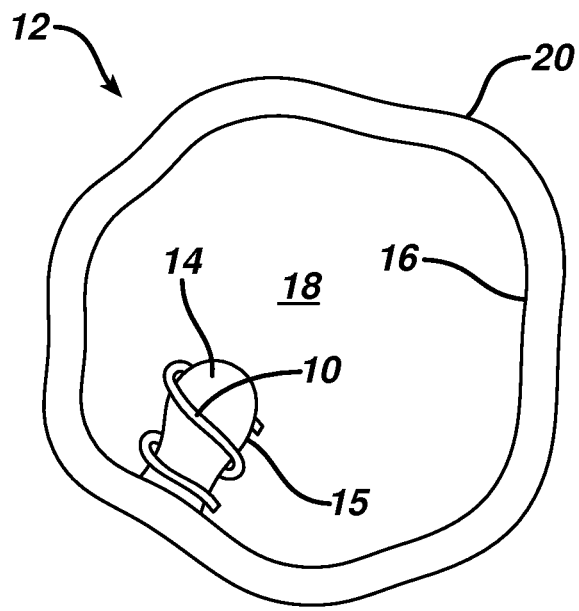
FIG. 4 is a cross-sectional view of one embodiment of a marking device disposed around tissue to be removed.

In yet another embodiment of marker placement shown in FIG. 4, the distance D can be zero and the marker 10 can directly engage the tissue 14 by extending around at least a portion of the tissue 14. In this embodiment, the marker 10 can extend at least partially around an outside surface 15 of the tissue 14 to be removed so as to not obstruct the body lumen's inner pathway 18 to any substantial extent beyond any obstruction caused by the tissue 14 itself, thereby allowing for normal functioning of the body lumen 12 when the marker 10 is disposed therein. In other words, if the marker 10 coils around at least a portion of the tissue 14, the marker 10 in the coiled position can take the shape of the tissue 14. Because the marker 10 in this embodiment does not extend around the inner wall 16 of the body lumen 12, the marker 10 may not be able to be palpably identifiable through the body lumen's outer surface 20. The marker 10 can still, however, be visually identified.

Once the marker 10 has been positioned in the coiled position in the body lumen 12, the distance D remains substantially unchanged until the marker 10 is absorbed by the body, the marker 10 is removed from the body, or the tissue 14 is removed from the body. In other words, the marker's position can be substantially static once the marker 10 is in the coiled position in the body lumen 12. In this way, the marker 10 can remain adjacent to the tissue 14 and accurately mark the location of the tissue 14 until the marker 10 is absorbed by the body, the marker 10 is removed from the body, or the tissue 14 is removed from the body.

The marker 10 can be introduced into the body lumen 12 to mark the tissue 14 in a variety of ways. Various devices can be used to deliver the marker 10 adjacent to the tissue 14, including rigid and flexible devices, such as elongate shafts configured to deliver the marker 10 to the tissue 14. The marker 10 can also be applied manually. In one embodiment, the marker 10 can be configured to be disposed in an expanded position within a channel of a delivery device. In the expanded position, the marker 10 can be generally elongated and uncoiled, although the marker 10 can generally follow the orientation of the delivery device and the delivery device's channel, and hence the marker 10 can curve or bend in the expanded position. The marker 10 can be biased to the coiled position such that when the marker 10 is advanced out the delivery device's distal end, the marker 10 can naturally transition from the expanded position to the coiled position. Because of the marker's bias to the coiled position, the marker 10 can have some bending or coiled biasing even in the expanded position but still be generally elongated. The diameter of the delivery device's pathway or cannulated interior can be chosen for a given marker's shape and size to be large enough to allow passage of the marker 10 but small enough to prevent the marker 10 from substantially moving into the coiled position within the delivery device.

Figure 5:
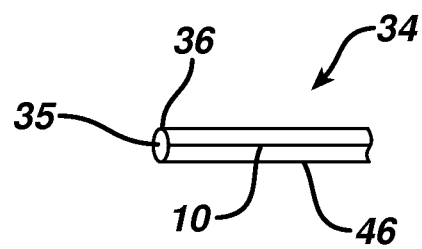
FIG. 5 is a perspective view of a distal portion of one embodiment of a delivery device having a marker disposed therein.

One embodiment of a delivery device 34 having the marker 10 disposed therein in the elongated position is shown in FIG. 5. The delivery device 34 can be a scoping device (e.g., an endoscope, laparoscope, and colonoscope), where the longitudinal channel 35 includes a working channel of the scoping device. Alternatively, the delivery device 34 can include virtually any surgical tool that has a cannulated interior and that is configured to be directly inserted into the body lumen 12 or inserted through an introducer device (e.g., through a working channel of a scoping device, through a trocar, etc.). In the event that the surgical tool used with the invention is a colonoscope, the delivery device 34 can be any flexible, elongate member that is capable of being inserted into the body, such as through a natural orifice, through a puncture hole formed in tissue, and in any other way appreciated by a person skilled in the art. In the illustrated embodiment, the delivery device 34 has an elongated shaft with a longitudinal channel extending therethrough. As shown, the marking device 34 has an elongate shaft 46. The elongate shaft 46 can have a variety of configurations, and the particular configuration can vary depending on the mode of insertion. In the illustrated embodiment, the elongate shaft 46 is disposed through a cannula having a working channel that extends into a body cavity. The elongate shaft 46 can also include one or more lumens formed therein and extending between proximal and distal ends thereof. The lumens can be used to deliver the marker 10 to the distal end 36 of the elongate shaft 46.

The marker 10 can be disposed within the delivery device 34 at any point before or after the delivery device 34 has been introduced into the body lumen 12, including before or after the delivery device 34 has been positioned at a desired position proximate to the tissue 14. Preferably, the marker 10 is advanced through the delivery device's working channel 35 after the tissue 14 to be marked has been located because in some surgical procedures, no tissue to be marked is located and hence no need exists to use the marker 10. Although, in some embodiments, the marker 10 can be pre-loaded into the delivery device 34.

Figure 6:
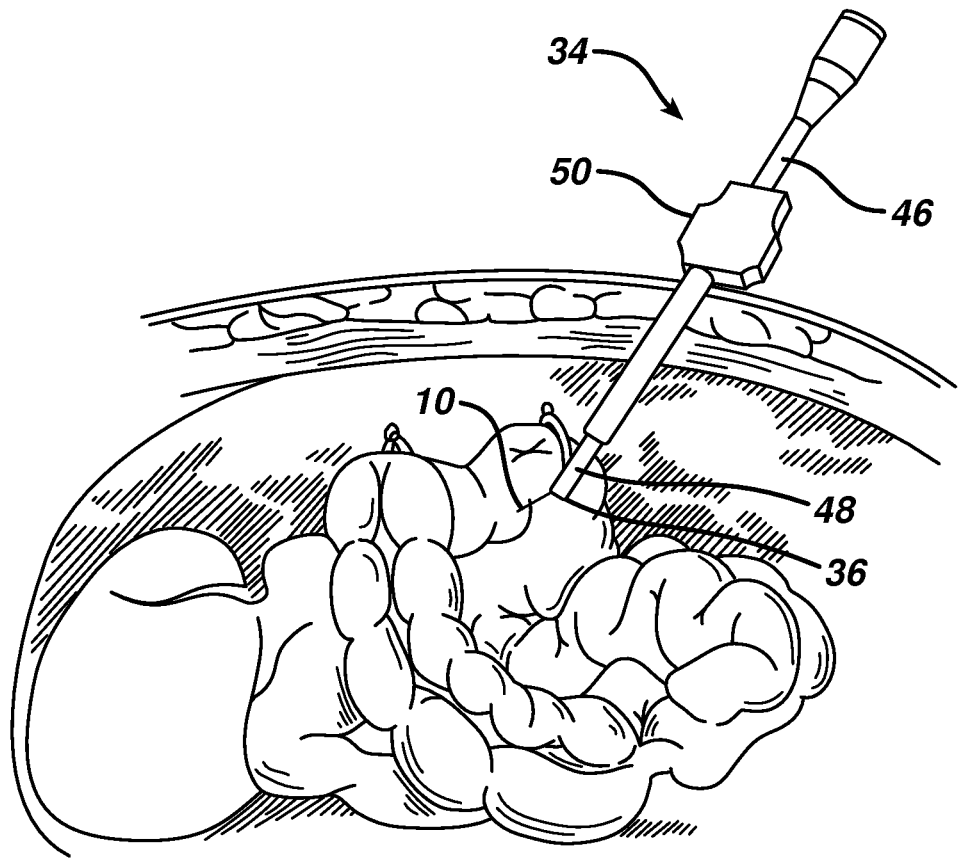
FIG. 6 is a perspective view of one embodiment of an introducer having the delivery device of FIG. 5 disposed therein.

FIG. 6 illustrates one exemplary embodiment of the delivery device 34 that is configured to be inserted in a body through a trocar 50. As shown, the delivery device 34 is inserted through the trocar 50 that extends through a tissue surface and into the abdominal cavity. As mentioned above, endoscopes or other introducer devices can also optionally be used, and/or the delivery device 34 can be an introducer that is directly inserted through a natural orifice or through a man-made orifice. Once positioned adjacent to a target tissue, the delivery device 34 can be manipulated using, for example, controls to articulate the distal end of the delivery device 34 and controls to advance the marker 10 out the distal end 36.

Figure 7:
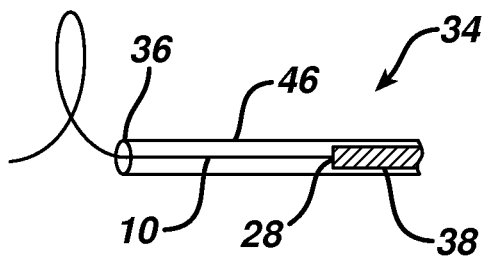
FIG. 7 is a perspective view of the delivery device and the marker of FIG. 5 showing the marker being advanced from the delivery device.

The marker 10 can be advanced from the delivery device 34 and into the body lumen 12 in a variety of ways. Generally, the marker 10 can be advanced through the delivery device 34 and out the delivery device's distal end 36, thereby moving from the expanded position inside the delivery device 34 and into the coiled position outside the delivery device 34. For example, as illustrated in FIG. 7, the marker 10 can be pushed out the distal end 36 of the delivery device 34, such as by manipulating the push rod or driver 38 disposed within the delivery device 34 proximal to the marker's proximal end 28. After the marker 10 has been advanced entirely into the body lumen 12, the marker 10 can be disengaged from the driver 38 if the marker 10 and the driver 38 are coupled, or the marker's proximal end 28 can merely abut the driver 38 such that movement of the driver 38 toward the delivery device's distal end 36 advances the marker 10 out of the delivery device's distal end 36. In some embodiments, the marker 10 may not be fully advanced into the body lumen 12. Rather, a portion of the marker 10 can be advanced into the body lumen 12, and when enough of the marker 10 is disposed in the body lumen 12 to sufficiently mark the tissue 14, the marker 10 can be cut (e.g., with a retractable knife at the delivery device's distal end 36 that can be actuated at the proximal end of the delivery device or introducer device) to leave a portion of the marker 10 within the delivery device 34. In this way, if multiple tissues need to be marked, the delivery device 34 can be advanced once into the introducer 30 with a length of marker material disposed therein, and multiple tissues can be marked using that one length of marker cut into two or more individual markers 10.

In another exemplary embodiment, illustrated in FIGS. 8-9, an introducer device 30, such as a colonoscope, can be introduced into the body lumen 12 and positioned proximate to the tissue 14. The introducer 30 includes at least one working channel 32 extending therethough that the marker 10 can be advanced through into the body lumen 12. As mentioned above, the marker 10 can be advanced directly through the introducer's working channel 32. Alternatively, as shown, the marker 10 can be disposed within the delivery device 34, and the delivery device 34 can be disposed and advanced through the introducer's working channel 32. Advancing the marker 10 through the delivery device 34 rather than directly through the working channel 32 of the introducer 30 can allow more flexibility and accuracy in positioning the marker 10 adjacent to the tissue 14 because the delivery device 34 is smaller than the introducer 30 and hence generally has easier maneuverability within the body lumen 12 than the introducer 30. The delivery device 34 can also be made from a material more flexible than a material used for the introducer 30, also allowing the delivery device 34 to be more easily positioned within the body lumen 12 than the introducer 30. Advancing the delivery device 34 through the introducer 30 can allow the delivery device 34 to be advanced beyond a distal end of the introducer 30 and into a viewing area of the introducer 30 so a surgeon can view the delivery device 34 and/or the marker 10 as the delivery device 34 and/or the marker 10 are being positioned.

The marker 10 and/or the delivery device 34 can be disposed within the introducer 30 at any point before or after the introducer 30 has been introduced into the body lumen 12, including before or after the introducer 30 has been positioned at a desired position proximate to the tissue 14. Preferably, the delivery device 34 is advanced through the introducer's working channel 32 after the tissue 14 to be marked has been located because in some surgical procedures, no tissue to be marked is located and hence no need exists to use the marker 10 and/or the delivery device 34. Although, in some embodiments, the delivery device 34 and/or the marker 10 can be pre-loaded into the introducer 30. Similarly, the marker 10 can be disposed in the delivery device 34 at any point before or after the delivery device 34 has been advanced through the introducer's working channel 32. Once the introducer 30 and/or the delivery device 34 have been positioned proximate to the tissue 14 to be marked, the marker 10 can be introduced into the body lumen 12, as shown in FIG. 9.

In another embodiment, the marker 10 can have a coil shape in the expanded position as well as in the coiled position. For example, as shown in FIG. 10, a marker 10' can be wrapped around a delivery device 34' (or any other device, such as an introducer device 30') in the expanded position as a coil having a first diameter D1. The marker 10' can be pushed or otherwise removed from the delivery device 34', such as by manipulating a push rod or driver 38' disposed within the delivery device 34' proximal to the marker's proximal end 28'. The marker 10' can optionally be coupled with the driver 38', e.g., by engaging with clips, clamps, an indentation in the driver 38' that the marker's proximal end 28' can fit into, or any other engagement mechanism. As the marker 10' moves off the delivery device 34', the marker 10' can transition from the expanded position to the coiled position, where the marker 10' is a coil having a second diameter D2 greater than or less than the first diameter D1, depending on the tissue to be engaged. For example, the marker 10' can be stretched around the delivery device 34' to the first diameter D1 that is larger than the naturally biased diameter of the marker 10' (which can be less than or equal to the second diameter D2) such that advancing off the delivery device 34' decreases the marker's diameter from D1 to D2. In this way, the marker 10' can be positioned, for example, above a tissue 14' extending from a lumen's inner wall 16' and be pushed off the delivery device 34' to decrease in diameter and coil around the tissue 14', such as in the example shown in FIG. 4. As another example, the marker 10' can be disposed within the delivery device 34' in a coiled position having one diameter and expand to a coiled position having a larger diameter as the marker 10' is advanced from the delivery device 34'.

In some embodiments, the marker 10 may not be biased to the coiled position, in which case the marker 10 can be introduced to the body lumen 12 in the expanded position and manually manipulated into the coiled position once it has been fully or partially introduced into the body lumen 12. For example, it may be desirable to manually engage the marker 10 with the tissue 14, e.g., by coiling the marker 10 around a tissue growth 14 as shown in FIG. 4. Furthermore, regardless of whether the marker 10 naturally moves from the expanded position to the coiled position or must be manually moved, the position of the marker 10 within the body lumen 12 can be manually adjusted using any appropriate tool (e.g., surgical instruments, one's fingertips, etc.) if, for example, the distance D between the marker 10 and the tissue 14 is too large or too small, the marker 10 has a kink in a coil, etc.

Figure 11:
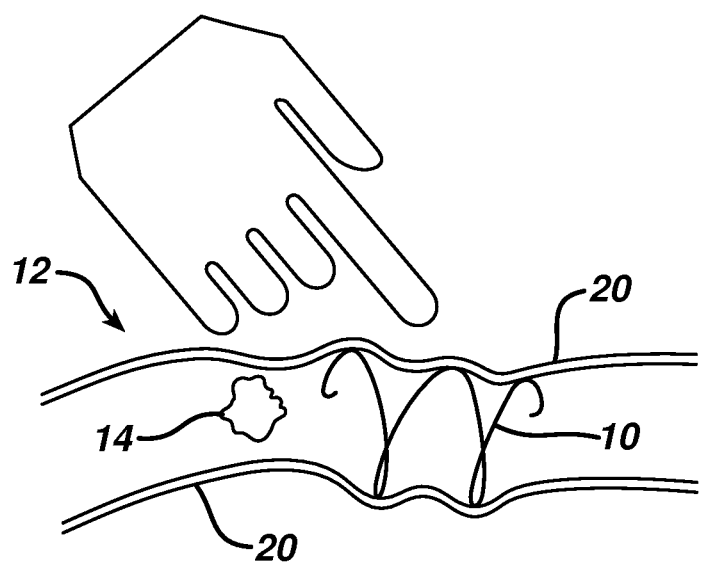
FIG. 11 is a perspective view of the marking device of FIG. 9 being palpably located in a body lumen.

Once the marker 10 has been disposed in the coiled position in the body lumen 12, the marker 10 can be left in the body lumen 12 after devices such as the introducer 30 and the delivery device 34 have been removed from the body lumen 12. The marker 10 can then be palpably identified, as illustrated in FIG. 11, to help locate the tissue 14. The marker 10 can be palpably identified directly on the body lumen's outer surface 20 as shown, or the marker 10 can be palpably identified through one or more layers of tissue adjacent to the body lumen's outer surface 20, e.g., from outside a patient's body. As mentioned above, the marker 10 can also or instead be visually identified.

The marker 10 can remain in the body lumen 12 for any length of time, e.g., twenty-four hours, two days, one week, three weeks, one month, etc. Being safe for use in the body, the marker 10 could remain inside the body lumen 12 indefinitely, but preferably, the marker 10 is either bioabsorbed or manually removed from the body after it has been used to locate the tissue 14. The length of time the marker 10 remains in the body lumen 12 can depend on any number of factors, such as the marker's material composition. Even if the marker 10 is bioabsorbable, the marker 10 can be removed from the body lumen 12 after it has been used to locate the tissue 14 and/or after the tissue 14 has been removed from the body lumen 12, during which procedure the marker 14 can also be removed from the body lumen 12.

Figure 12:
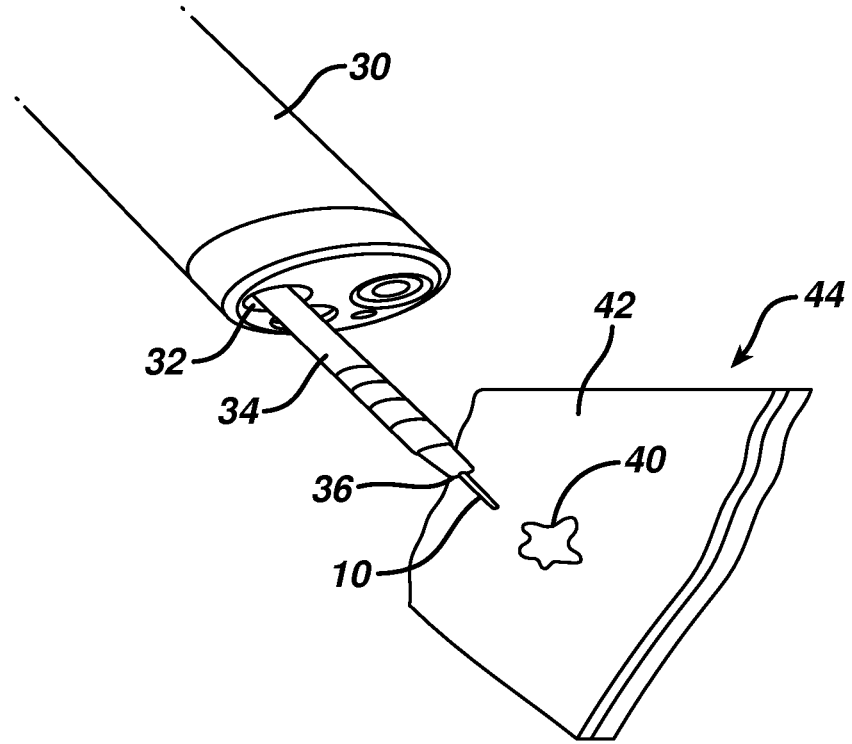
FIG. 12 is a perspective view of another embodiment of an applicator for applying a marker to a tissue.

If the marker 10 is not being used to mark tissue in a tubular structure but to otherwise mark tissue on a tissue surface, the marker 10 can function and be introduced to tissue in a way similar to any way described above. For example, as illustrated in FIG. 12, the marker 10 can be used to mark a tissue growth 40 on a surface 42 of an organ 44. The marker 10 can be disposed in the delivery device 34, which can be disposed in the working channels 32 of the introducer 30, and the marker 10 can be advanced to the tissue surface 42 from the delivery device's distal end 36. The marker 10 can then coil adjacent to the tissue growth 40, either naturally or manually.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for marking tissue, comprising:
    advancing a delivery device into a body lumen;
    advancing a marker from the delivery device to deliver the marker into the body lumen, the marker moving from an expanded position to a coiled position as it is advanced from the delivery device to form a coil that engages an inner surface of the body lumen and expands the body lumen, the marker in the coiled position having a maximum diameter greater than an inner diameter of an unexpanded portion of the body lumen so as to not substantially obstruct an inner pathway of the body lumen; and
    after the coil engages the inner surface of the body lumen and expands the body lumen, identifying a location of the marker by palpating an external surface of the body lumen.

2. The method of claim 1, wherein the marker is delivered proximate to tissue to be removed from the body lumen.

3. The method of claim 2, wherein identifying the location of the marker in the body lumen includes locating tissue to be removed from the body lumen.

4. The method of claim 1, further comprising removing the delivery device from the body lumen, and leaving the marker in the coiled position inside the body lumen.

5. The method of claim 1, wherein the coil extends around the inner surface of the body lumen and expands an inner wall of the body lumen and an outer surface of the body lumen.

6. The method of claim 1, wherein the coil is positioned on the inner surface of the body lumen proximate to a tissue growth on the body lumen.

7. The method of claim 1, further comprising introducing the delivery device to the body lumen through a cannula having a working channel extending into the body lumen.

8. The method of claim 7, wherein the cannula comprises a colonoscope.

9. The method of claim 1, wherein when the marker is in the expanded position, the marker has a substantially straightened, elongate configuration.

10. The method of claim 1, wherein the marker engages the inner surface of the body lumen without puncturing the body lumen.

11. A method for marking tissue, comprising:
    advancing a coiled marker along a delivery device disposed adjacent to tissue in a body to advance the marker off of a distal end of the delivery device, the marker contracting as it is removed from the delivery device so as to reduce an inner diameter of the coiled marker, the coiled marker engaging an inner wall of a tubular structure proximate to tissue to be removed from the body;
    wherein, when the coiled marker engages the inner wall of the tubular structure, the coiled marker has a diameter that is larger than an inner diameter of the tubular structure so as to not substantially obstruct an inner pathway of the tubular structure.

12. The method of claim 11, wherein, when the marker engages the inner wall of the tubular structure, the marker at least partially extends around tissue to be removed from the body.

13. The method of claim 11, wherein when the marker engages the inner wall of the tubular structure, the marker extends around tissue to be removed from a surface of an organ.

\* \* \* \* \*